United States Patent
Boese et al.

(10) Patent No.: US 7,778,690 B2
(45) Date of Patent: Aug. 17, 2010

(54) METHOD FOR LOCATING A MEDICAL INSTRUMENT DURING AN INTERVENTION PERFORMED ON THE HUMAN BODY

(75) Inventors: Jan Boese, Eckental (DE); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 481 days.

(21) Appl. No.: 11/805,215

(22) Filed: May 22, 2007

(65) Prior Publication Data

US 2007/0276227 A1  Nov. 29, 2007

(30) Foreign Application Priority Data

May 24, 2006  (DE) .................. 10 2006 024 425

(51) Int. Cl.
*A61B 5/05* (2006.01)
*H01J 35/00* (2006.01)
(52) U.S. Cl. ................... 600/424; 600/425; 378/126
(58) Field of Classification Search ............. 600/407, 600/424; 378/162
See application file for complete search history.

(56) References Cited

U.S. PATENT DOCUMENTS 6,317,621 B1   11/2001  Graumann et al.

| 2005/0245807 A1 | 11/2005 | Boese et al. |
| 2005/0281385 A1 | 12/2005 | Johnson et al. |
| 2007/0276216 A1 * | 11/2007 | Beyar et al. ................. 600/407 |

FOREIGN PATENT DOCUMENTS

| DE | 199 19 907 A1 | 11/2000 |
| DE | 697 26 415 T2 | 9/2004 |
| DE | 10 2004 004 620 A1 | 8/2005 |
| EP | 1 593 343 A2 | 11/2005 |
| WO | WO 01/87136 A2 | 11/2001 |
| WO | WO 2005/082246 A1 | 9/2005 |

* cited by examiner

*Primary Examiner*—Eric F Winakur
*Assistant Examiner*—Michael T Rozanski

(57) ABSTRACT

The invention relates to a method for locating a medical instrument during an intervention performed on the human body using an X-ray image recording system and an electromagnetic locating system whose systems of coordinates have been or will be mutually registered, with a first item of positional information about the instrument being obtained continuously by means of the locating system and in each case two two-dimensional X-ray images positioned at an angle to each other being intermittently recorded by means of the X-ray image recording system, from which images a second item of positional information about the instrument is determined and compared with the first item of positional information, after which the first item of positional information will be corrected depending on the comparison result taking account of the second item of positional information obtained from the X-ray images.

20 Claims, 2 Drawing Sheets

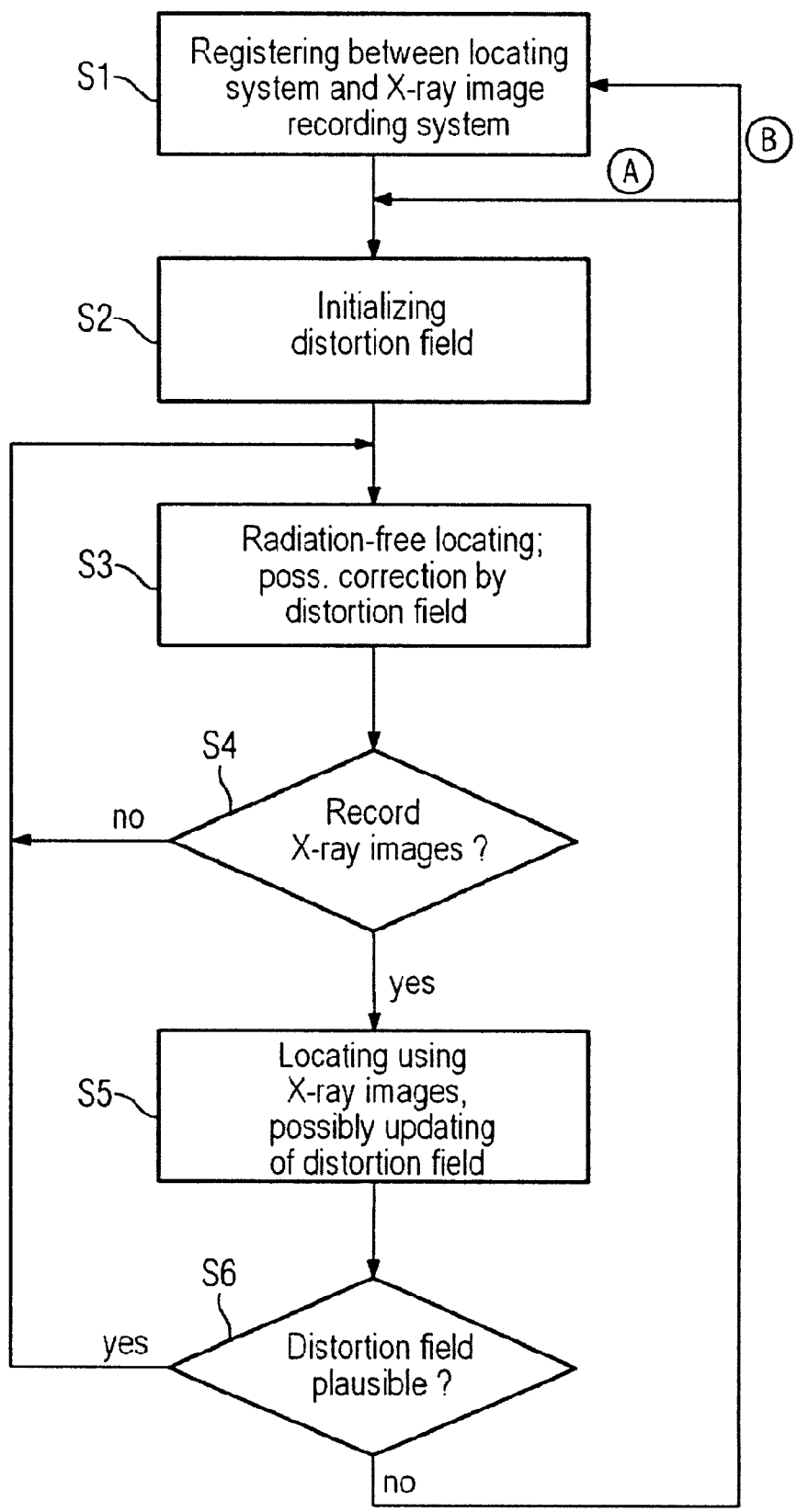

METHOD FOR LOCATING A MEDICAL INSTRUMENT DURING AN INTERVENTION PERFORMED ON THE HUMAN BODY

CROSS REFERENCE TO RELATED APPLICATIONS is application claims priority of German application No. 10 2006 024 425.7 filed May 24, 2006, which is incorporated by reference herein in its entirety.

FIELD OF THE INVENTION

The invention relates to a method for locating a medical instrument during an intervention performed on the human body.

BACKGROUND OF THE INVENTION

Medical instruments, for example catheters, are introduced into the human body during interventional and diagnostic procedures for a variety of purposes. Electrophysiological procedures on the heart are a known instance. It is important during procedures of said kind to know the momentary position of the medical instrument.

A known method for locating the medical instrument therein provides for recording two X-ray images of the region at the intervention site that are recorded at different angles and both show the medical instrument, and for determining and, where applicable, displaying the three-dimensional position of the medical instrument through back projection. However, said type of locating based on fluoroscopy has the disadvantage that both the patient and attendant medical personnel will be exposed to a high radiation dose because the X-ray images have to be recorded very often to keep track of the medical instrument. Said method has nonetheless remained in use as it exhibits a high degree of accuracy in position determining.

To reduce the patient's and medical personnel's exposure to radiation, alternative systems have been proposed that are not based on fluoroscopy.

A first group of said type of locating systems provides for one or more microcoils on the tip of the medical instrument. Provided outside the body are at least three stationary coils via which an electromagnetic signal is sent. The received signal from which the medical instrument's position can be determined through determining the distances from the transmitter coils and triangulation is measured.

In a second group of locating systems, catheters normally employed for obtaining intracardial ECG signals are used for electrophysiology. Three roughly orthogonally arranged pairs of external electrodes to which defined alternating voltages are successively applied are therein adhesively attached to the patient's skin. Through measuring the voltage on the catheter it is possible to determine the impedance between it and the skin electrodes and thus make an approximate inference about the distance. Again through triangulation, the medical instrument's position can be determined from distances from all three pairs of electrodes.

However, the cited X-ray-free locating systems both have the disadvantage that locating accuracy is limited. In contrast to the fluoroscopic methods, where an accuracy in the submillimeter range can be achieved, only accuracies in the range of 0.5 to 5 mm are achieved with the electromagnetic coil-based methods; errors in the centimeter range can occur in the case of the impedance-measuring systems.

Apart from by the patient's movements, particularly in the case of impedance measurements, said locating errors are caused in both groups of locating systems by distortions in the electromagnetic or, as the case may be, electric field. With the first group, errors are produced mainly by conducting materials such as metals in the area surrounding the patient. Metal parts of said type are, for example, an X-ray tube and a detector of an additionally present X-ray system. Complex calibrating techniques have been proposed for compensating said distortions and hence for achieving greater accuracy.

In the second group, the distortion in the field is due to the differing conductivity of different types of tissue etc. (fat, blood, lung tissue, etc.). That results in a non-linear voltage drop between the skin electrodes. Alongside extremely difficult local calibrating by means of instruments having a plurality of electrodes at a known distance, the use of reference electrodes has been proposed for compensating said effect, with its being possible in the latter case only to determine relative distances.

SUMMARY OF THE INVENTION

The object of the invention is thus to disclose a method for locating a medical instrument, which method will allow more accurate position determining with low exposure to radiation and without the use of complex calibrating techniques.

To achieve said object it is provided in the case of a method for locating a medical instrument during an intervention performed on the human body for an X-ray image recording system and an electromagnetic locating system to be used whose systems of coordinates have been or will be mutually registered, with a first item of positional information about the instrument being obtained continuously by means of the locating system and in each case two two-dimensional X-ray images positioned at an angle to each other being intermittently recorded by means of the X-ray image recording system, from which images a second item of positional information about the instrument is determined and compared with the first item of positional information, after which the first item of positional information will be corrected depending on the comparison result taking account of the second item of positional information obtained from the X-ray images.

The invention thus proposes beneficially combining the advantages of an electromagnetic locating system, with which the patient and medical personnel will not be subjected to extreme radiation exposure, and of an X-ray image recording system, which will enable a high degree of accuracy to be achieved in position determining, by obtaining the position of the medical instrument basically continuously by means of the locating system and intermittently checking said position using the X-ray image recording system. X-ray images will consequently need to be recorded far less frequently, with the result that the exposure to radiation will be substantially reduced. The extent to which the locating system's positional information is still reliable is nevertheless routinely checked by producing X-ray recordings and determining a second item of positional information. In addition to the two coordinate systems' being registered, a correction will be determined on the basis of said positional information if deviations in the positions that have been determined exceed a specific threshold, which correction will then be applied accordingly so that the medical instrument's position can continue being determined with a high degree of accuracy. The correction undertaken is therein to be understood as being continuous, meaning that with account being taken of the second item of positional information obtained from the X-ray images the first item of positional information will, in the event of a deviation in the positions determined by the locating system and X-ray image recording system, be continuously corrected until the next check is performed by recording two further X-ray images, so that correct positional information will be available to the user.

The accuracy of X-ray-free locating systems will consequently be improved by means of the inventive method and applications that are very demanding in terms of accuracy may be rendered realizable for the first time. The X-ray dose to which the patient and medical personnel are exposed will be greatly reduced compared to pure locating by means of an X-ray image recording system.

For implementing correcting it can be provided according to the invention for a distortion field describing on a localized basis the deviation in the position determined from the first item of positional information from the actual position that can be determined by means of the X-ray image recording system to be used for correcting the first item of positional information and, when the X-ray images have been recorded, for said field to be adjusted depending on the comparison result taking account of the second item of positional information.

A particularly advantageous embodiment of the inventive method is described thereby. As already explained above, apart from in possible patient movements, the reasons for the inaccuracies in the locating system's first item of positional information are to be found in the spatially changeable electromagnetic fields at the intervention site. If it is established during the comparison that the medical instrument's positions respectively determined from the first item of positional information and from the second item of positional information deviate from each other, then said deviation will have been determined for the instrument's momentary location. Because further X-ray images are intermittently recorded and the instrument is at other locations at each of those instants, the relevant deviations can also be determined—if present— for said other locations. The invention is therein based on the knowledge that because said deviations are due specifically to the electromagnetic field inhomogeneities at said locations they are in the final analysis a localized measure of said very field distortions. Based on said distortions, a distortion field is then appropriately adjusted in line with the new deviation information each time X-ray images are recorded followed by a comparison. The distortion field is a vector field that assigns each point in space a three-dimensional vector indicating the difference between the second and first item of positional information. For the locations at which there is no deviation information, that can be done using suitable interpolation techniques. While the locating system is operating continuously, so also when no X-ray images are being recorded, the first items of positional information will be continuously corrected by adding the respective differential vector of the distortion field so that the effects of the electromagnetic field distortions will be approximately computed out again.

Said type of mathematical operation can therein be permanently provided taking account of a distortion field in the actual implementation. The distortion field at the start of locating with registered systems of coordinates will then first be initialized such that the mathematical operation is an identity operation. That means that, because no deviation information is known, the first item of positional information will initially be accepted in uncorrected form. With the intermittent recording of X-ray images by means of the X-ray image recording system the deviation information will be determined at various locations by way of the comparison and will be reflected in the appearance of the distortion field, which will be adjusted accordingly. Included therein, of course, is that no correction will take place if the respectively measured positions concur, meaning if there is no deviation.

The first item of positional information can particularly advantageously be taken into account for determining the second item of positional information at the time the X-ray images are recorded. That is based on the knowledge that the deviations in the locating system's first items of positional information from the X-ray image recording system's second items of positional information move within a specific range, meaning that the respectively determined positions are close to each other. That will allow reliable position determining even if a medical instrument is difficult to detect in the X-ray images. It can for that purpose be expediently provided for only a predetermined area around the position, ensuing from the first item of positional information, within the X-ray images to be considered for determining the second item of positional information. Said area will then, for example, be defined as the maximum deviation to be expected. It can alternatively also be provided for the position described by the first item of positional information to be used as the starting point for searching for the medical instrument in the X-ray images.

Various criteria can be provided for initiating recording of the X-ray images. Thus it can be provided for X-ray images to be recorded at regular, predetermined intervals. The required or expedient intervals therein vary as a function of the intervention. If, for instance, a neurological examination is being performed on the head, with that being clamped rigidly in position to prevent movements on the part of the patient, then it will be perfectly adequate for the intermittent recording of X-ray images to take place at intervals ranging from minutes to one hour. In the case, though, of cardiac examinations where the first item of positional information is obtained at a frequency of around 50 Hz, it can be provided for X-ray images to be recorded intermittently every second.

Alternatively or in addition, X-ray images can also be recorded under the control of a user. If the first items of positional information appear unreliable to the user, he/she will then be able to initiate checking and correcting or, as the case may be, improving of the correction himself/herself.

If there are large field distortions in the region of the intervention it can also be provided for X-ray images to be recorded after the medical instrument has traveled a certain distance or, as the case may be, the position has changed by a certain distance, which can be expedient especially when a distortion field is used since the field distortions will then be as it were mapped and can be imaged in the distortion field.

In certain circumstances it may be necessary for the systems of coordinates to be reregistered during the intervention if a reregistering condition occurs. A reregistering condition of said type can be, for example, too large a correction. It will then be expedient to mutually reregister the two systems, namely the locating system and X-ray image recording system. Such an eventuality may, for example, arise if the patient moves. Reregistering of said type can also be initiated by a user having seen a necessity therefore. It is, though, especially advantageous for the correction, particularly the distortion field, to undergo a plausibility check on the basis of the result of which reregistering of the systems of coordinates will be initiated. If, for example, a distortion field is used, then it will be known that its purpose is in the final analysis to represent the field distortions in the electromagnetic field. The conditions applying to an electromagnetic field of said type or, as the case may be, its distortions can also be checked for the correction. Thus a field of said type must be smooth and the distortions ought not to be particularly large. It is therefore scrutinized within the plausibility check whether the correction, in particular the distortion field, is then consistent with the recordings forming the basis of these causes. Reregistering can thereby advantageously also be initiated automatically. It can in the same manner also be automatically checked whether the deviations established during the comparison have become excessive.

For fundamentally reregistering the locating system's and X-ray image recording system's systems of coordinates based on which the deviation information is during the comparison determined based on the first and second item of positional information there are several procedural modes that depend on the specific embodiment of the medical examination and/or therapy device designed for implementing the method. If both the X-ray image recording system and locating system are a fixed constituent of said device, whose geometric relationship is fixed, then it will suffice to reregister the systems of coordinates at regular maintenance intervals. In that case the locating system is usually a coil-based locating system. The transmitter coils, whose signal is to be received by the microcoil on the medical instrument, are then attached to the device in a stationary manner. The necessary corrections here result in reality for the most part from the distortions in the electromagnetic field.

Another situation arises when, although including stationary components, meaning ones not secured to the patient, the locating system first has to be combined with the X-ray image recording system as the two systems are used jointly only occasionally or are separate functional units. The systems of coordinates will then have to be reregistered each time the locating system changes position relative to the X-ray image recording system. The greatest deviations likely during the intervention are here, though, too—provided the systems' relative positions remain the same—to be expected as a result of the distortion in the electromagnetic field.

With locating systems whose system of coordinates is in the final analysis patient-linked such as, for example, impedance-measuring systems where the electrodes are attached to the patient externally, the systems of coordinates have to be registered prior to each intervention after the patient has been emplaced and the locating system set up. It is therein particularly to be noted that reregistering will in many cases be necessary if the patient moves and the consequent deviations cannot be adequately compensated by the correction. That is one of the cases in which reregistering can be necessary during an intervention.

As already mentioned, a coil-based locating system can be used as the locating system. It is therein frequently provided for, in addition to the instrument, a reference coil that is stationary relative to the body to be inserted therein or attached externally thereto. Said coil will not change its position relative to the body. If said type of reference coil is used, then the first item of positional information and second item of positional information about said reference coil can also be expediently determined and taken into account for the correction. A third item of positional information about the instrument relative to the body can moreover also be determined therefrom. Movements of the body itself can hence in the final analysis be tracked by way of a reference coil of said type. That will in turn make it possible at any time to determine the medical instrument's position within a system of coordinates moving with the patient's body. Determining a position of said kind will be particularly expedient when a preoperative image dataset is available in which the instrument can be shown. The third item of positional information can then be used for that purpose.

As an alternative thereto an impedance-measuring system can also be employed as the locating system. As already indicated above, it is therein expedient to register the systems of coordinates at each intervention before the first item of positional information is being continuously obtained.

A biplanar system can advantageously be employed as the X-ray image recording system. The X-ray images positioned at an angle to each other can be recorded simultaneously by means of a biplanar system of said type, for example an X-ray system having two C-arms.

Attention is further drawn at this point to the fact that more than two X-ray images can, of course, also be recorded for determining the position more accurately.

BRIEF DESCRIPTION OF THE DRAWINGS

Further advantages and specifics of the present invention will emerge from the exemplary embodiments described below and with reference to the drawings, in which:

FIG. 3 is a flowchart of the inventive method.

DETAILED DESCRIPTION OF THE INVENTION

Figure 1:
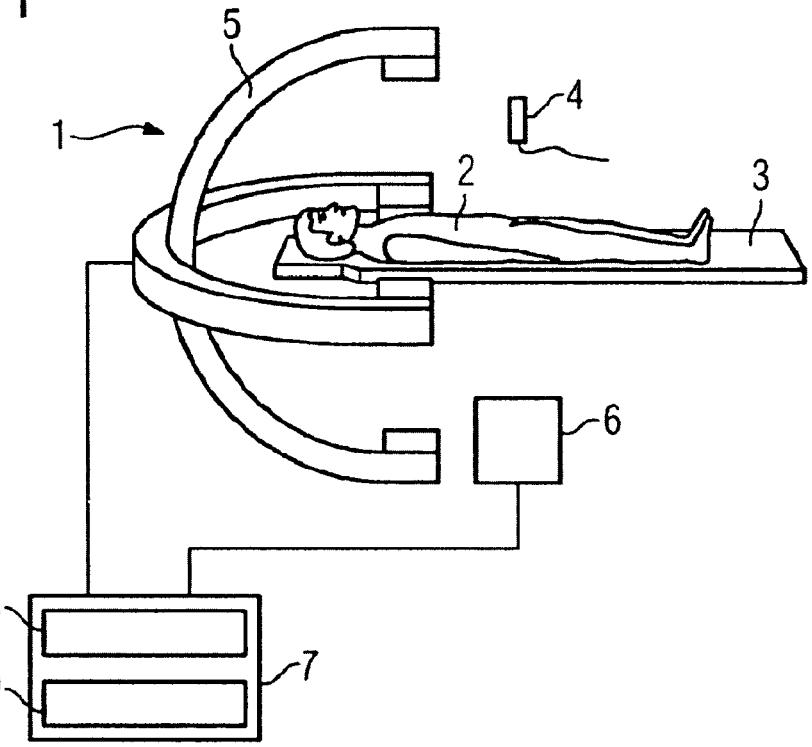
FIG. 1 shows a medical examination and/or therapy system embodied for implementing the inventive method.

FIG. 1 shows by way of example the basic components of an examination and/or therapy system 1 embodied for automatically implementing the inventive method. A patient 2 is located on a patient table 3 during the intervention so that a target area into which a medical instrument 4 is to be inserted is located within the recording area of an X-ray image recording system 5, here embodied as a biplanar X-ray device. In this case mutually perpendicular X-ray images of the patient 2 can be recorded therewith. Further provided is an electromagnetic locating system 6 that is only roughly indicated here. It can be a coil-based locating system or an impedance-measuring system. Both the X-ray image recording system 5 and the locating system 6 communicate with a computing device 7 that includes an evaluation computer 8 and an error-correcting computer 9. The computing device 7 is therein embodied for implementing the inventive method.

Figure 2:
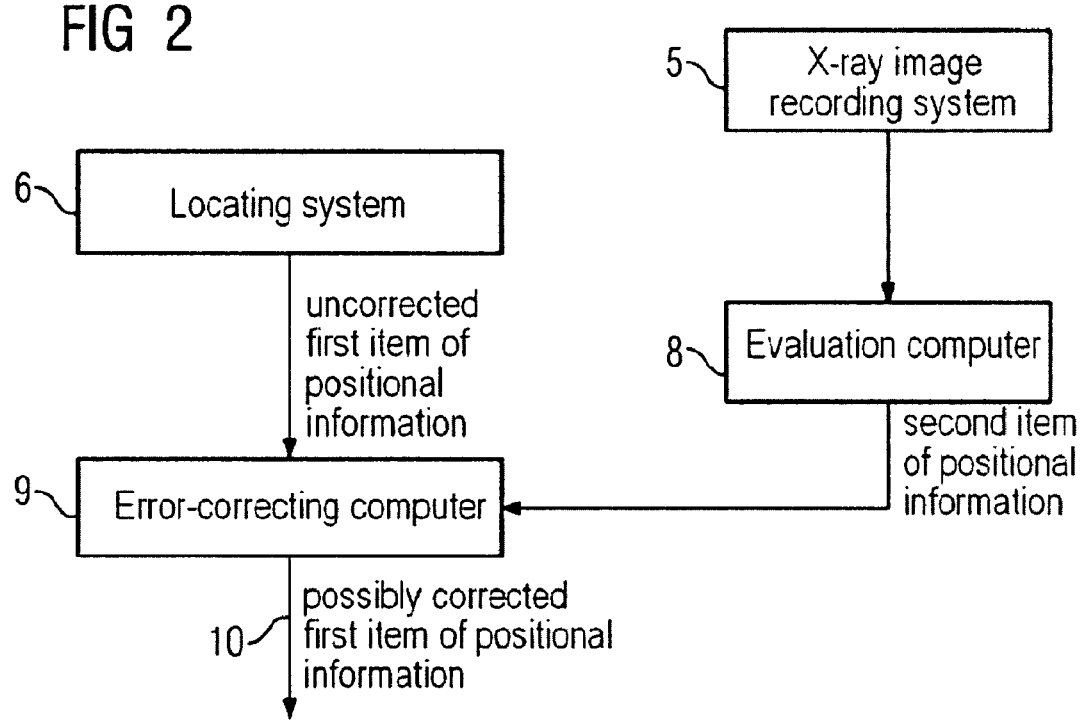
FIG. 2 is a schematic sketch showing how the components interact.

FIG. 2 shows in the form of a schematic sketch how the individual components of the examination and/or therapy system 1 interact. First items of positional information about the medical instrument 4 are continuously recorded by the locating system 6 during the intervention. Said first, measured item of positional information is transferred to the error-correcting computer 9. If no X-ray images have yet been recorded or if no deviation requiring to be corrected has been established between the position determined from the second items of positional information relating to the X-ray images and the position determined from the first items of positional information, then the first items of positional information will not be changed by the error-correcting computer 9. Two X-ray images positioned at an angle to each other and whose data is transferred to the evaluation computer 8 are, though, recorded intermittently by the X-ray image recording system 5. Through back projecting, the evaluation computer 8 determines therefrom the second item of positional information that indicates the position of the medical instrument 4 visible in both X-ray images. The position determined from the first item of positional information and the position determined from the second item of positional information can be compared on the basis of the existing registration of the systems of coordinates of the locating system 6 and X-ray image recording system 5. That is done by the error-correcting computer 9. If the comparison result is a deviation requiring to be corrected, then the deviation information will be put to future use for appropriately correcting the first item of positional information, as is indicated by arrow 10.

FIG. 3 is a flowchart of the inventive method. Registering is first carried out at step S1 between the locating system 6 and X-ray image recording system 5. Said registering does not have to be performed immediately prior to every intervention; that will depend mainly on the equipment used. Essentially three instants are to be distinguished at which registering can take place. If there is a functional unit having a locating system 6 in the case of which the first item of positional information is measured in a system of coordinates that is fixed relative not to the patient but to space, and if there is a fixed geometric relationship between the components defining the system of coordinates that is fixed relative to space and the X-ray image recording system 5, then it can suffice for registering to take place at adequate, lengthy intervals, for example during a maintenance operation once a year.

Matters are different when, although the locating system 6 determines the first item of positional information in a spatially fixed manner, the locating system 6 and X-ray image recording system 5 are separate functional units first having to be combined for one or more interventions. The two systems' systems of coordinates will then be registered at the time of combining.

If, finally, the locating system 6 is, as in the case of, for instance, impedance-measuring systems, one that measures within a system of coordinates fixed relative to the patient, then the patient will have to be positioned in as immobile a manner as possible relative to the X-ray image recording system 5. The electrodes, for example, will then be attached and registration measuring performed. The medical instrument 4 will in the case of an impedance-measuring system already have been inserted into the body of the patient 2 for that purpose.

In the first two cited instances, particularly when a coil-based locating system 6 is used, registering is to be seen as rigid, meaning that it will not usually be disrupted even if the patient 2 moves. Registering in the last-cited instance is, though, dependent on the position of the patient 2 because, for example, the reference electrodes will move jointly with the patient 2.

A distortion field will then be initiated at step S2 at the start of locating, so usually when the intervention begins. The purpose of the distortion field is on a localized basis to indicate, when relevant deviation information is available, the extent to which the position determined from the first item of positional information and the actual position (the position ensuing at measuring points from the second item of positional information) of the medical instrument 4 mutually differ there. As it is initially assumed that no such deviation has occurred, meaning that the relationship between the systems of coordinates will precisely supply the position in the other system of coordinates, the distortion field will be initialized in such a way as to supply the identity matrix at each location. If the distortion field is consequently applied to a first item of positional information, said field will initially remain unchanged.

Radiation-free locating is then first performed at step S3, meaning that the further used determined position of the medical instrument 4 in the human body will be determined from the first item of positional information. The distortion field consisting hitherto of identity matrices, the first item of positional information will remain unchanged. The positional information obtained about the medical instrument 4 can be used for, for example, a presentation or display on, for instance, a monitor, but it can also be otherwise further processed.

A check is carried out during continuous locating with the aid of the radiation-free locating system 6 to determine whether a condition exists for intermittent recording of the X-ray images. That is done at step S4. Various possibilities that can also be applied in combination are conceivable as a condition of such type. It is firstly possible for X-ray images to be required to be recorded for the first time immediately at the start of the intervention or, as the case may be, locating operation in order to determine a displacement already present when measuring begins in the positions determined by the locating system 6 and X-ray image recording system 5.

It can in accordance therewith or independently thereof be provided for a new intermittent recording of X-ray images to be required to take place in each case after specific intervals. It is alternatively conceivable for a certain distance traveled or the distance from the last location point at which X-ray images were recorded to serve as the criterion for an intermittent recording of X-ray images.

It is finally possible with the inventive method for a user himself/herself, if having noticed signs that the position, ensuing from the first item of positional information, of the medical instrument 4 could not be correct, to initiate a recording of X-ray images via, for example, an appropriate input means. If it is not required for X-ray images to be recorded at that time, then the first item of positional information will keep being continuously obtained, meaning that step S3 will be repeated again. If it is decided at step S4 that an intermittent recording of X-ray images is to take place, then the method will be continued at step S5.

Two X-ray images positioned at an angle to each other are at step S5 first recorded by the X-ray image recording system 5. The medical instrument 4 can be seen in both X-ray images. It is therein in part difficult or time-consuming actually to detect the medical instrument 4 in the X-ray images. The first item of positional information from the locating system 6 is, though, according to the method taken as the starting point for the search and/or as delimiting it. The first item of positional information is thus, based on the registration, first translated into the system of coordinates of the X-ray image recording system 5. An area in which the medical instrument 4 will be sought automatically around the transferred position ensuing from the momentary first item of positional information is then determined in the X-ray images. The size of said area is determined by the largest deviation that is to be expected. The region in which the medical instrument 4 has to be sought in the X-ray images will in that way be limited, as a result of which the search will be simplified and shortened.

If the medical instrument 4 has been detected in both X-ray images, then its position, and consequently the second item of positional information, can be determined through back projection. The first item of positional information and the second item of positional information are then compared. The result of said comparison can be either a deviation in the positions determined by the systems 5 and 6, or else parity or an insignificant deviation.

The distortion field will, where applicable, be updated based on said comparison and on the first or, as the case may be, second item of positional information. The distortion field will need no updating only if a relevant deviation between the determined positions has hitherto not occurred at any location. The distortion field will in all other cases be updated. The chief sources of the inaccuracies in the locating system 6 being field distortions in the electromagnetic field (apart from movements of the body when a locating system 6 is used having a system of coordinates fixed relative to the patient), what will in the final analysis result as a localized distortion field after a few of the intermittent recordings is a map of said field distortions causing the deviations. The established absence of a deviation will accordingly also be relevant information if a deviation has previously been established at another location. The distortion field will then, for example through interpolation, be adjusted such that correcting will continue being performed at the other location while there will be none at the present location exhibiting no deviation. The flow of correcting operations between said locations is suitably modeled aided by the basic knowledge that what is being used is a map of electromagnetic field distortions.

An interesting supplement emerges when in the case of impedance-measuring systems a reference instrument is used that is sited at a location fixed relative to the patient's body. That instrument will also supply positional information and can be located by means of the X-ray images. As it is stationary relative to the patient's body, its change in position, advantageously registered over time, will provide information about movements of the patient, which information can also be taken into account here. The reference instrument will moreover provide further information about a deviation at another location, namely the reference instrument's. Account can advantageously also be taken of that information.

A similar situation arises when in the case of a coil-based locating system a reference coil is employed. It must, though, then be noted that the coordinates of the reference coil that is stationary relative to the patient's body will also be determined in the coil-based locating system's system of coordinates that is fixed relative to space. Information about the reference coil and the deviation at its location can, of course, nevertheless be taken into account when the distortion field is being updated. Movements of the patient are here modeled by the reference coil directly, so in the locating system's system of coordinates itself, with its being possible, owing to said reference coil, to constantly track said movements also during continuous locating at step S3. Said information is extremely important since with its aid it is possible, for example, to move the localized distortion field, which of course represents field distortions at specific locations fixed relative to space, with the body. In this way, also, the reference coil's positional information will be taken into account in determining the distortion field.

Incidentally, reference coils of said type moreover serve also to determine a position of the medical instrument 4 relative to the body of the patient 2. Information of said kind in a system of coordinates relating to the patient 2 can be useful in, for example, showing the medical instrument 4 in a preoperatively recorded image dataset specific to the intervention area.

When step S5 has been completed, a check is performed at step S6 to determine whether the distortion field is plausible. This formulation is to be understood in the broadest possible sense. The distortion field's plausibility can be checked by way of a user's impressions or an automated plausibility check can be carried out. Thus, as one possibility, a user can decide manually by operating a suitable input means whether the distortion field is correct or, as the case may be, still adequate. Thus it may be necessary in the event of, for instance, a larger movement performed by the patient 2 or a conspicuous measuring error to reregister the systems of coordinates of the locating system 6 and X-ray image recording system 5 or, as the case may be, reinitialize the distortion field.

There are several aspects to the automatic plausibility check. It is based on the well-founded assumption that the distortion field in the final analysis models electromagnetic field distortions. These are, though, subject to certain limitations that will be automatically checked within the scope of the plausibility check. Thus the field must be smooth and not exhibit excessive deviations. If the relevant criteria are not met, for example if there are excessively large corrections, then the plausibility check will identify the distortion field as being implausible.

If the distortion field is identified at step S6 as being plausible, then a branch will again be made back to step S3 where continuous locating and determining of the first item of positional information will be resumed. If the distortion field has since been adjusted, meaning that a correction is necessary, then the first items of positional information will be corrected by means of a suitable mathematical operation with the aid of the distortion field.

If the distortion field is identified at step S6 as being implausible, then there will in the final analysis be two possibilities. If there is an above-mentioned rigid registration at step S1, meaning if the geometric correlations between the locating system 6 and X-ray image recording system 5 are fixed so that there is in any event also a fixed relationship between their systems of coordinates, then a branch will be made back to step S2, as is indicated by arrow A. If, though, no such rigid registration exists, then the systems of coordinates will be reregistered and the method will branch back to step S1 in accordance with arrow B.

The invention claimed is:

1. A method for locating a medical instrument during an intervention performed on a live body, comprising:
   continuously obtaining a first position information of the instrument in the body by a locating system;
   intermittently recording two two-dimensional X-ray images of the body by an X-ray image recording system with a coordinate system of the X-ray image recording system being registered with a coordinate system of the locating system;
   determining a second position information of the instrument in the body from the X-ray images;
   comparing the second position information with the first position information;
   correcting the first position information based on the comparison; and
   performing the intervention according to the corrected first position information of the instrument.

2. The method as claimed in claim 1, wherein the X-ray images are recoded relative to each other by an angle.

3. The method as claimed in claim 1, wherein a distortion field describes a deviation between the second position information of the instrument determined from the X-ray images and the first position information of the instrument located by the locating system and is adjusted based on the comparison.

4. The method as claimed in claim 1, wherein the second position information of the instrument is determined from the X-ray images according to the first position information of the instrument located by the locating system.

5. The method as claimed in claim 4, wherein the second position information of the instrument is determined in the X-ray images only from an area around the first position information of the instrument within the X-ray images.

6. The method as claimed in claim 1, wherein the X-ray images are recorded at a regular and predetermined interval or by a control of a user.

7. The method as claimed in claim 1, wherein the coordinate system of the X-ray image recording system is re-registered with the coordinate system of the locating system during the intervention if a re-registration condition occurs.

8. The method as claimed in claim 7, wherein the re-registration is initiated by a user or based on a plausibility check of the correction.

9. The method as claimed in claim 1, wherein the locating system is a coil-based locating system.

10. The method as claimed in claim 9, wherein a reference coil is inserted into the body or attached externally to the body and stationary relative to the body.

11. The method as claimed in claim 10, wherein the first and the second position information of the instrument relative to the reference coil are determined and used in the correction.

12. The method as claimed in claim 11, wherein a third position information of the instrument relative to the body is determined and the instrument is shown in a preoperative image dataset based on the third position information of the instrument.

13. The method as claimed in claim 1, wherein the locating system is an impedance-measuring system.

14. The method as claimed in claim 13, wherein a reference instrument is located at a fixed position relative to the body to detect a movement of the body and a deviation between the first and the second position information of the instrument.

15. The method as claimed in claim 1, wherein the coordinate system of the X-ray image recording system is registered with the coordinate system of the locating system before the first position information of the instrument is obtained.

16. The method as claimed in claim 1, wherein the X-ray imaging recording system is a biplanar system.

17. A device for locating a medical instrument during an intervention performed on a live body, comprising:
  a locating system that continuously obtains a first position information of the instrument in the body;
  an X-ray image recording system that intermittently records two two-dimensional X-ray images of the body with a coordinate system of the X-ray image recording system being registered with a coordinate system of the locating system; and
  a computing device that:
    determines a second position information of the instrument in the body from the X-ray images,
    compares the second position information with the first position information, and
    corrects the first position information based on the comparison.

18. The device as claimed in claim 17, wherein the X-ray images are recoded relative to each other by an angle.

19. The device as claimed in claim 17, wherein the locating system is a coil-based locating system or an impedance-measuring system.

20. The device as claimed in claim 17, wherein the X-ray imaging recording system is a biplanar system.

* * * * *